United States Patent [19]

Böhner et al.

[11] Patent Number: 4,792,608
[45] Date of Patent: Dec. 20, 1988

[54] PYRIMIDIN-5-YLSULFONAMIDES

[75] Inventors: Beat Böhner, Binningen; Werner Föry, Basel; Rolf Schurter, Binningen; Georg Pissiotas, Lörrach, all of Switzerland

[73] Assignee: Ciba-Geigy Corporation, Ardsley, N.Y.

[21] Appl. No.: 90,262

[22] Filed: Aug. 26, 1987

Related U.S. Application Data

[62] Division of Ser. No. 842,618, Mar. 21, 1986, Pat. No. 4,707,551, which is a division of Ser. No. 496,325, May 19, 1983, Pat. No. 4,612,037.

[30] Foreign Application Priority Data

May 28, 1982 [CH] Switzerland ............ 3314/82-2

[51] Int. Cl.⁴ .......................... C07D 239/32
[52] U.S. Cl. .................... 544/319; 544/298
[58] Field of Search ......... 544/319, 322, 326, 317, 544/298

[56] References Cited

U.S. PATENT DOCUMENTS 3,787,410  1/1974  Anderson et al. ............ 544/317

FOREIGN PATENT DOCUMENTS 5058209  5/1975  Japan .

OTHER PUBLICATIONS

Gilow, et al. vol. 28, 1944–1998 (1962).
Daiichi Seiyaku Co. Ltd. Chemical Abst. vol. 97, 33372d (1982).
Gilow et al, Chemical Abst. vol. 59, 6408b (1963).
Herak et al, Chemical Abst. vol. 67, 77769y (1967).
Anderson et al, Chemical Abst. vol. 77; 126702p (1972).
Anderson et al. Chemical Abst. vol. 80, 83037t (1974).

Primary Examiner—Donald G. Daus
Assistant Examiner—Cecilia Shen
Attorney, Agent, or Firm—Kevin T. Mansfield; Edward McC. Roberts

[57] ABSTRACT

The invention relates to novel sulfonylureas of the formula I

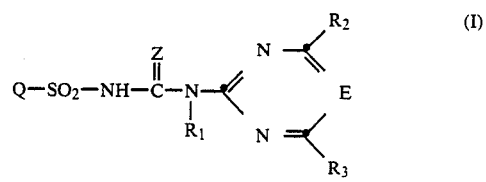

wherein
$R_1$ is hydrogen or $C_1$-$C_5$alkyl,
$R_2$ and $R_3$, each independently of the other, are hydrogen, $C_1$-$C_5$alkyl, $C_1$-$C_5$alkoxy, $C_1$-$C_5$alkylthio, $C_1$-$C_5$haloalkyl, halogen, $C_1$-$C_5$haloalkylthio, $C_1$-$C_4$alkylamino, $C_1$-$C_4$dialkylamino, an alkoxyalkyl group or alkoxyalkoxy group, each containing not more than 6 carbon atoms,
Z is oxygen or sulfur,
E is —CH= or —N=, and
Q is an unsubstituted or substituted 6-membered heterocyclic radical containing 2 to 3 nitrogen atoms and bound through a carbon atom,
and the salts thereof.

A process for the preparation of the novel compounds and the use thereof are also described. The compounds of formula I can be used in the form of agriculturally useful compositions for controlling weeds and/or for selectively influencing plant growth.

3 Claims, No Drawings

PYRIMIDIN-5-YLSULFONAMIDES

This is a division of application Ser. No. 842,618 filed on Mar. 21, 1986 now U.S. Pat No. 4,707,551 which is a division of application Ser. No. 496,325 filed on May 19, 1983 now U.S. Pat. No. 4,612,037.

The present invention relates to a group of novel sulfonylureas and sulfonylthioureas which have valuable growth regulating properties and which are suitable for selectively influencing plant growth, for the control of weeds e.g. in crops of useful plants and/or for influencing the phytotoxic properties of other herbicidal compounds. The invention also relates to the preparation of these sulfonylureas and sulfonylthioureas, and to agricultural compositions which contain them.

Accordingly, the invention relates to compounds of the formula I

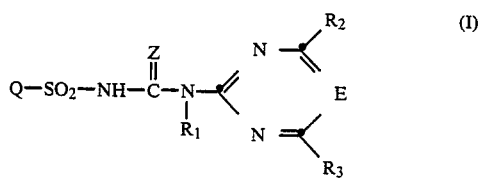

wherein $R_1$ is hydrogen or $C_1$-$C_5$alkyl, $R_2$ and $R_3$, each independently of the other, are hydrogen, $C_1$-$C_5$alkyl, $C_1$-$C_5$alkoxy, $C_1$-$C_5$alkylthio, $C_1$-$C_5$haloalkyl, halogen, $C_1$-$C_5$haloalkylthio, $C_1$-$C_4$alkylamino, $C_1$-$C_4$dialkylamino, an alkoxyalkyl group or alkoxyalkoxy group, each containing not more than 6 carbon atoms, Z is oxygen or sulfur, E is —CH= or —N=, and Q is an unsubstituted or substituted 6-membered heterocyclic radical containing 2 to 3 nitrogen atoms and bound through a carbon atom, and the salts thereof.

Depending on the indicated number of carbon atoms, alkyl by itself or as moiety of another substituent will be understood as meaning e.g. the following groups: methyl, ethyl, propyl, butyl or pentyl and the isomers thereof such as isopropyl, isobutyl, tert-butyl, isopentyl etc. Haloalkyl denotes a monohalogenated or perhalogenated alkyl radical, e.g. $CF_3$, $CH_2Cl$, $CCl_3$, $CHCl_2$, $CH_2I$, $C_2H_4Br$, $CH_2Br$ etc. Throughout this specification, halogen denotes fluorine, chlorine, bromine or iodine, with fluorine, chlorine or bromine being preferred. Agriculturally suitable salts are e.g. those which the compounds of formula I form with amines, alkaline metal bases or alkaline earth metal bases, or with quaternary ammonium bases. Suitable alkali metal or alkaline earth metal bases will be understood as meaning here in particular the hydroxides, such as lithium, sodium, potassium, magnesium or calcium hydroxide.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Typical substituents of the radical Q in formula I are: halogen, pseudohalogen, nitro, alkyl, haloalkyl, alkoxy, alkylthio, haloalkoxy, haloalkylthio, amino, alkylamino, dialkylamino, alkylcarbonylamino, alkylcarbonyl, alkoxycarbonyl, alkylthiocarbonyl, carbamoyl, alkylaminocarbonyl, dialkylaminocarbonyl, alkylsulfinyl, alkylsulfonyl, alkenyloxy, alkynyloxy, and the following groups such as phenyl, phenoxy or phenylthio, which are unsubstituted or substituted by halogen, nitro, cyano, alkyl, alkoxy, haloalkyl or haloalkoxy, and also benzyl or benzyl substituted by halogen and/or alkyl. Preferred substituents are those containing not more than 6, preferably not more than 4, carbon atoms in the aliphatic moiety.

The following 6-membered heterocyclic radicals Q are typical substituents within the scope of this invention: pyrimidine, pyridazine, pyrazine and triazine, with pyrazine being preferred.

The heterocyclic radical Q may be unsubstituted or contain one or more substituents.

The compounds of formula I are biologically active oils, resins or solids which are stable at room temperature and have very valuable growth regulating, in particular, growth inhibiting, properties. They can therefore be used in agriculture or related fields for selectively reducing the growth of monocot and dicot plants. Depending on the mode of application or on the rate of application, the compounds act as selective or total herbicides.

A preferred group of compounds of formula I comprises those compounds wherein Z is oxygen and $R_1$ is hydrogen.

A particularly preferred group of compounds of formula I comprises those compounds wherein $R_1$ is hydrogen, each of $R_2$ and $R_3$ independently of the other is $C_1$-$C_3$alkyl, $C_1$-$C_3$alkoxy, $C_1$-$C_3$haloalkyl, $C_1$-$C_3$haloalkoxy, halogen or $C_2$-$C_4$alkoxyalkyl, Z is oxygen, E is nitrogen or CH, Q is a heterocyclic radical as defined for formula I which is unsubstituted or substituted by a member selected from chlorine, bromine, fluorine, nitro, cyano, $C_1$-$C_4$alkylcarbonyl, $C_1$-$C_4$alkoxycarbonyl, $C_1$-$C_3$alkoxy, $C_1$-$C_3$alkylthio, $C_3$-$C_5$alkoxyalkoxy, $C_1$-$C_3$-alkylsulfinyl, $C_1$-$C_3$alkylsulfonyl, $C_1$-$C_4$alkyl, trifluoromethyl, trichloromethyl, $C_1$-$C_4$cyanoalkyl, $C_2$-$C_4$alkenyloxy, $C_3$-$C_4$alkynyloxy or N-$C_1$-$C_4$alkylcarbonylamino.

Particularly preferred individual compounds are:

N-(2-methylpyrazin-3-ylsulfonyl)-N'-(4-methoxy-6-methyl-1,3,5-triazin-2-yl)urea and N-(2-methoxypyrazin-3-ylsulfonyl)-N'-(4-methoxy-6-methyl-1,3,5-triazin-2-yl)urea.

The compounds of formula I may be prepared in a manner known per se in an inert organic solvent or mixture of solvents.

The compounds of formula I may be prepared as follows in accordance with equation [1]

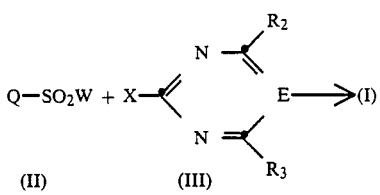

by reacting a phenylsulfonyl derivative of the formula II with a compound of the formula III, wherein X and W are $-NH_2$, $-N=C=Z$ or $-NR_1-CZ-OR$ groups, the substituents $R_1$, $R_2$, $R_3$, Q, Z and E are as defined for formula I, R is an aliphatic or atomatic radical, preferably $C_1-C_4$alkyl, phenyl or benzyl, with the proviso that the reactants of the formulae II and III are also so chosen that an amino function reacts either with an isocyanato or isothiocyanato function or with the $[-NR_1-CZ-OR]$ group.

The process is conveniently carried out in the presence of a base. It can often be of advantage to carry out the reaction in an inert gas atmosphere, e.g. under nitrogen. The process for preparing the compounds of formula I is an object of the invention.

If desired, the compounds of formula I may be converted into basic, agriculturally suitable addition salts by reaction with amines, alkali metal hydroxides or alkaline earth metal hydroxides, or with quaternary ammonium bases. This is accomplished e.g. by reacting a compound of formula I with an equimolar amount of base and removing the solvent by evaporation. Such reactions, and also the preparation of individual starting materials of the formula III, are known and described e.g. in U.S. Pat. Nos. 3,384,757 and 3,410,887.

The starting compounds of the formula III are known or they are prepared by methods which are known per se.

Some of the compounds of formula II, wherein W is $NH_2$, are known. The novel compounds of formula II have been specially developed for synthesising the compounds of formula I. They therefore constitute an object of the invention.

The starting compounds of formula II, wherein W is $-NH-CZ-OR$, are novel and have been specially developed for synthesising the compounds of formula I. They therefore also constitute an object of the invention. They are prepared by methods which are known per se.

The sulfonamides of the formula II can be prepared by reacting the corresponding sulfonyl chlorides or sulfonyl fluorides with ammonia or ammonium hydroxide solutions (see e.g. J. Chem. Soc. Perkin Trans. 1, 1972, 522).

The isocyanates of the formulae II and III can be prepared by phosgenating the corresponding amino compounds, in the presence of butylisocyanate and in a chlorinated hydrocarbon as solvent, at reflux temperature. Reference is made in this connection to "Neuere Methoden der präparativen organischen Chemie", Vol. VI, pp. 211-229; Verlag Chemie, Weinheim, 1970. When using thiophosgene, isothiocyanates of the formulae II and III are obtained in corresponding manner.

The isothiocyanates of formula II are also prepared by treating the sulfonamides of formula II with carbon disulfide and potassium hydoxide and subsequently phosgenating the dipotassium salt [see Arch. Pharm. 299, 174 (1966)].

Compounds of the formulae II and III, wherein W and X are the $-NR_1-CZ-OR$ group, can be obtained from the corresponding amino compounds by reaction with a haloformate or halothioformate of the formula IV

or with a dicarbonate or dithiocarbonate of the formula V

wherein Hal is halogen, preferably chlorine or bromine, Z is oxygen or sulfur and R is an aliphatic or aromatic radical, preferably $C_1-C_4$alkyl, phenyl or benzyl. This reaction is preferably conducted in the presence of a base.

The starting amines of the formula III are known or they can be prepared by per se known methods of synthesising heterocyclic amines (see "The Chemistry of Heterocyclic Compounds", Vol. XVI, Interscience Publishers, New York, London, in which methods of synthesising 2-aminopyridines and of 2-amino-1,3,5-triazines may be found).

These reactions are conveniently carried out in aprotic, inert organic solvents such as methylene chloride, tetrahydrofuran, acetonitrile, dioxan, or toluene.

The reaction temperatures are preferably in the range from $-20°$ to $+120°$ C. The reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The compounds of formula I are stable compounds which are of low toxicity to man and animals.

When preparing the compounds of formula I in accordance with equation [1], isomeric reaction products of the formulae Ia and Ib

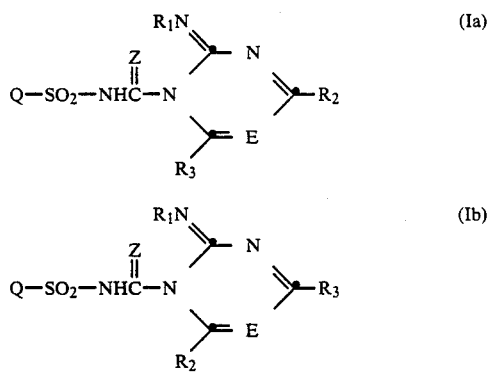

can be isolated in certain cases by addition of a compound of formula II to a ring nitrogen atom of a compound of formula III. In the formulae Ia and Ib above, $R_1$, $R_2$, $R_3$, Q, Z and E are as defined for formula I. These isomeric compounds Ia and Ib also influence plant growth. Accordingly, all agrochemically useful compounds and compound mixtures which are obtained by reacting compounds of formula II with compounds of formula III also fall within the province of the present invention. Sulfonylureas containing two to three nitrogen atoms in the 6-membered heterocyclic radical Q are novel.

Surprisingly, it has been found that the novel compounds of formula I have good selective herbicidal properties and are therefore suitable for use in crops of cultivated plants. Moreover, it can also be observed that some of the compounds even damage problem weeds which up to now have only been controlled with total herbicides.

A number of the compounds of formula I are translocatable, i.e. they are absorbed at the treated site of the plant (leaf, stem, root etc.) and transported to other sites where they exert their action. In doing so, they not only follow the path of nutrient transport from the roots to the leaves, but also conversely penetrate to the roots from the leaves. Thus with the aid of this translocatability, e.g. by means of a surface treatment, it is possible to damage perennial weeds to their roots. Furthermore, compared with conventional herbicides, the compounds of formula I are effective even when used in very low rates of application.

In addition, the compounds of formula I are able to potentiate the phytotoxic action of other herbicides against certain noxious plants and to reduce the toxicity of such herbicides to some cultivated plants. This can lead to a lowering of the total concentration of herbicide and consequently to a reduced environmental impact.

If the rates of application are further lowered, then the growth regulating properties of the compounds of formula I predominate. The compounds exert a selective action on the plant metabolism, which results in particular in a reduction of the vegetative growth often in favour of the generative growth. This selective influence on the physiological processes of plant development makes the compound of formula I useful for different purposes, especially for those in connection with labour-saving in measures taken in crops of cultivated plants or for increasing yield.

The compounds of formula I disclosed herein can be used as herbicides and/or as growth regulators. Previous experience with growth regulators has shown that the active ingredients are able to induce one or more different responses in the plants. These different responses depend largely on the time of application, i.e. on the development stage of the seed or plant, on the mode of application, and in particular on the concentrations employed. Such responses differ in turn, however, depending on the species of plant. Accordingly, the application of compounds of formula I affords the possibility of influencing the growth of plants in the desired manner.

Vegetative plant growth is inhibited with the novel compounds of the formula I or with the compositions containing them. By means of this growth inhibition the compounds of the invention are able to increase substantially the yield of plants. Thus the vegetative growth of e.g. soybean plants and other leguminosae such as beans, peas or lentils is reduced in favour of the generative growth, whereby a direct increase in yield is achieved. The vegetative growth of other species of plants, e.g. of vines, cereals, grasses and ornamentals, is also inhibited in desired manner. In addition, a significant strengthening of the supporting tissue of the treated plants is observed.

An interesting manner of influencing plant growth derives from the special property of the compounds of formula I of selectively influencing the growth of specific plants, especially cereals. This selective growth inhibition substantially increases the breaking strength of the plants while the yield remains unchanged, thereby providing a very interesting method of protecting plant crops from lodging caused by storms or prolonged rainfall. Further, selective inhibition of the vegetative growth of many cultivated plants permits more plants to be grown per unit of crop area, resulting in a significant increase in yield with the same fruit setting and in the same crop area. The use of growth inhibitors also brings about a more effective utilisation of nutrients which are then able increasingly to promote flower formation and fruiting. In this manner, higher yields are achieved while the amount of waste vegetative plant residues (e.g., straw, potato foliage, beet leaves) is simultaneously reduced.

To be singled out for special mention is also the possibility of inhibiting the formation of shoots in different types of plants, especially tobacco plants, whenever the main shoot has been pruned shortly before flowering with the object of increasing the growth of the leaves.

Accordingly, the present invention relates to the use of the compounds of formula I as herbicides and/or growth regulators. The invention also relates to a method of controlling weeds pre- and postemergence, of inhibiting the growth of monocot and dicot plants, especially of grasses, cereals and tobacco suckers, as well as of increasing the yield of leguminous plants.

The compounds of the formula I are used in unmodified form, or preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumic, broken brick, sepiolite or bentonite; and suitable non-sorbent carriers are materials such as calcite or sand. In addition, a great number of pregranulated materials of inorganic or organic nature can be used. e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp. Ridgewood, N.J., 1979, and Sisley and Wood, "Encyclopedia of Surface Active Agents", Chemical Publishing Co., Inc. New York, 1964.

The pesticidal compositions usually contain 0.1 to 95%, preferably 0.1 to 80%, of a compound of the formula I, 1 to 99.9% of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders: | |
| active ingredient: | 0.5 to 90%, preferably 10 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end users will normally employ dilute formulations. The formulations can be diluted to a concentration as low as 0.001%. The rates of application are normally from 0.01 to 10 kg a.i./ha.

The compositions may also contain further ingredients, such as stabilisers, antifoams, viscosity regulators, binders, tackifiers as well as fertilisers or other active ingredients in order to obtain special effects.

The invention also relates to agriculturally suitable compositions which contain at least one compound of formula I as active ingredient.

Furthermore, the present invention relates to a process for the preparation of such compositions, which comprises intimately mixing the active ingredient with one or more substances or groups of substances described herein. The invention also relates to a method of treating plants, which comprises applying thereto the compounds of formula I or the novel compositions containing them.

In the following Examples parts and percentages are by weight.

PREPARATORY EXAMPLE
EXAMPLE 1

(a) 3-Chloropyridazine-6-sulfonamide

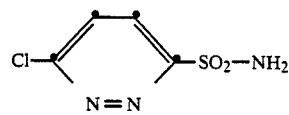

A suspension of 20 g of 3-chloropyridazine-6-thiol and 54.4 g of potassium hydrogen fluoride in 200 ml of 50% acetic acid is cooled to 0° C. With vigorous stirring, chlorine is then introduced into the suspension at 0°-5° C. over 3 hours. The sulfonyl chloride is precipitated from the reaction mixture by addition of 300 ml of cold water, isolated by filtration, and washed with cold water. In the meantime, a sulfonating flask is charged with an excess of ammonia. The sulfonyl chloride is then added, in portions, with stirring. The reaction mixture is stirred for several hours, diluted with 100 ml of cold water, and insoluble constituents are removed by filtration. The filtrate is adjusted to pH 4 with dilute hydrochloric acid and then filtered, affording 11 g of the compound of the above formula with a melting point of 150°-152° C. (decomposition).

(b) N—(3-Chloropyridazine-6-sulfonyl)phenylcarbamate

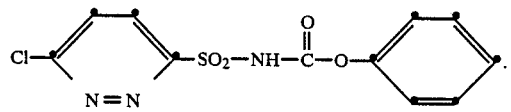

To a solution of 10.6 g of 3-chloropyridazine-6-sulfonamide in 50 ml of dimethylformamide are added, under nitrogen and at room temperature, 2.5 g of a 55% dispersion of sodium hydride in oil in portions over 15 minutes. After a further 15 minutes at 35° C., the reaction mixture is cooled to 25° C. and then 12.4 g of diphenyl carbonate are added to the solution. The reaction mixture is stirred for 2 hours at room temperature and then poured into a mixture of 500 ml of ice/water and 50 ml of hydrochloric acid. The precipitate is filtered with suction, washed with cold water and dried in a vacuum cabinet, affording 14.4 g of the compound of the above formula with a melting point of 136° C.

(c) N—(3-Chloropyridazine-6-sulfonyl)-N'—(4-methoxy-6-methyl-1,3,5-triazin-2-yl)urea

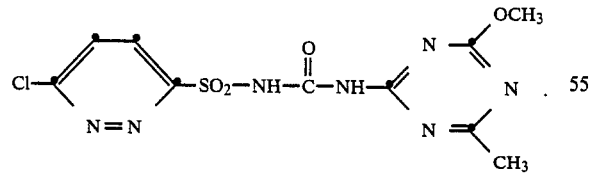

A mixture of 14.2 g of N-(3-chloropyridazine-6-sulfonyl)phenylcarbamate and 6.3 g of 2-amino-4-methoxy-6-methyl-1,3,5-triazine are refluxed for 1 hour in 120 ml of absolute dioxan. When the reaction is complete, the mixture is concentrated in vacuo and the residue is taken up in a saturated aqueous solution of sodium bicarbonate and the insoluble constituents are extracted with methylene chloride. The aqueous phase is acidified with dilute hydrochloric acid and extracted with methylene chloride. The methylene chloride solution is dried over sodium sulfate and concentrated, affording 7 g of the compound of the above formula with a melting point of 135° C.

The intermediates and final products listed in the following tables can be prepared in corresponding manner:

TABLE 1

Q—SO$_2$—NH$_2$

| Compound | Q | Abbreviation | Physical data |
|---|---|---|---|
| 1.1 | (pyrimidine with CH$_3$) | Q 1 | m.p. 109–110° C. |
| 1.2 | (pyrimidine with OCH$_3$) | Q 2 | m.p. 115–120° C. |
| 1.3 | (pyridine N) | Q 3 | |
| 1.4 | (pyridine N) | Q 4 | |
| 1.5 | (CH$_3$ pyridine) | Q 5 | |
| 1.6 | (CH$_3$, H$_3$C pyridine) | Q 6 | |
| 1.7 | NH—CO—CH$_3$ | Q 7 | |

TABLE 1-continued

Q—SO₂—NH₂

| Compound | Q | Abbreviation | Physical data |
|---|---|---|---|
| 1.8 | pyridazine with OCH₃ | Q 8 | |
| 1.9 | pyridazine with H₃C | Q 9 | |
| 1.10 | pyridazine with Cl | Q 10 | |
| 1.11 | pyridazine with OCH₃ and Cl | Q 11 | |
| 1.12 | pyridazine with H₃CO and Cl | Q 12 | |
| 1.13 | pyridazine with Cl, Cl | Q 13 | |
| 1.14 | pyrimidine with Cl, Cl | Q 14 | |
| 1.15 | pyrimidine with Cl | Q 15 | |
| 1.16 | pyrimidine with OCH₃ | Q 16 | |
| 1.17 | pyrimidine with OCH₃, OCH₃ | Q 17 | |
| 1.18 | pyrazine with CH₃, H₃C | Q 18 | |
| 1.19 | pyrazine with H₃C | Q 19 | |
| 1.20 | pyrimidine with CF₃ | Q 20 | |
| 1.21 | pyrimidine with C₂H₅, H₅C₂ | Q 21 | |
| 1.22 | triazine with H₃C | Q 22 | |
| 1.23 | triazine with H₃C | Q 23 | |

TABLE 1-continued

Q—SO₂—NH₂

| Compound | Q | Abbreviation | Physical data |
|---|---|---|---|
| 1.24 | 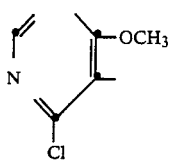 pyrimidine with OCH₃ and Cl | Q 24 | |
| 1.25 | 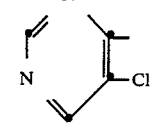 pyrimidine with Cl | Q 25 | |
| 1.26 | 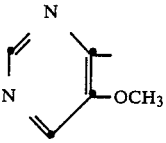 pyrimidine with OCH₃ | Q 26 | |
| 1.27 | 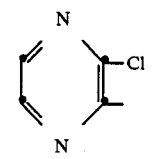 pyrazine with Cl | Q 27 | |
| 1.28 | 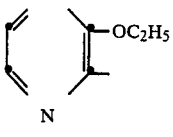 pyrazine with OC₂H₅ | Q 28 | |
| 1.29 | 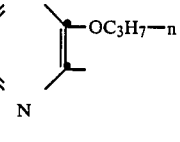 pyrazine with OC₃H₇—n | Q 29 | |
| 1.30 | 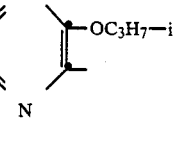 pyrazine with OC₃H₇—i | Q 30 | |
| 1.31 | 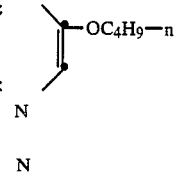 pyrazine with OC₄H₉—n | Q 31 | |
| 1.32 | 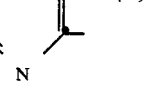 pyrazine with OC₄H₉—i | Q 32 | |
| 1.33 | 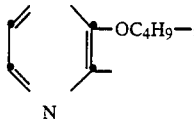 pyrazine with OC₄H₉—s | Q 33 | |
| 1.34 | 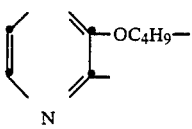 pyrazine with OC₄H₉—t | Q 34 | |
| 1.35 | 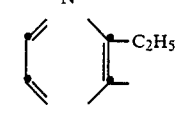 pyrazine with C₂H₅ | Q 35 | |
| 1.36 | 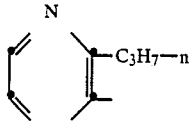 pyrazine with C₃H₇—n | Q 36 | |
| 1.37 | 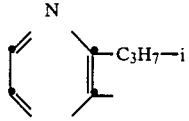 pyrazine with C₃H₇—i | Q 37 | |
| 1.38 | 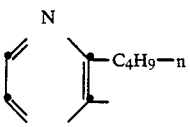 pyrazine with C₄H₉—n | Q 38 | |
| 1.39 | 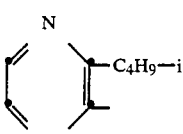 pyrazine with C₄H₉—i | Q 39 | |

TABLE 2

Q—SO₂—W

| Compound | Q | W | Physical data |
|---|---|---|---|
| 2.1 | Q 1 | —NH—CO—OCH₃ | |
| 2.2 | Q 2 | —NH—CO—OCH₃ | |
| 2.3 | Q 3 | —NH—CO—OCH₃ | |
| 2.4 | Q 4 | —NH—CO—OCH₃ | |
| 2.5 | Q 5 | —NH—CO—OCH₃ | |
| 2.6 | Q 6 | —NH—CO—OCH₃ | |
| 2.7 | Q 7 | —NH—CO—OCH₃ | |
| 2.8 | Q 8 | —NH—CO—OCH₃ | |
| 2.9 | Q 9 | —NH—CO—OCH₃ | |
| 2.10 | Q 10 | —NH—CO—OCH₃ | |
| 2.11 | Q 11 | —NH—CO—OCH₃ | |
| 2.12 | Q 12 | —NH—CO—OCH₃ | |
| 2.13 | Q 13 | —NH—CO—OCH₃ | |
| 2.14 | Q 14 | —NH—CO—OCH₃ | |
| 2.15 | Q 15 | —NH—CO—OCH₃ | |

TABLE 2-continued

| Compound | Q | W | Physical data |
|---|---|---|---|
| 2.16 | Q 16 | —NH—CO—OCH₃ | |
| 2.17 | Q 17 | —NH—CO—OCH₃ | |
| 2.18 | Q 18 | —NH—CO—OCH₃ | |
| 2.19 | Q 19 | —NH—CO—OCH₃ | |
| 2.20 | Q 20 | —NH—CO—OCH₃ | |
| 2.21 | Q 21 | —NH—CO—OCH₃ | |
| 2.22 | Q 22 | —NH—CO—OCH₃ | |
| 2.23 | Q 23 | —NH—CO—OCH₃ | |
| 2.24 | Q 24 | —NH—CO—OCH₃ | |
| 2.25 | Q 25 | —NH—CO—OCH₃ | |
| 2.26 | Q 26 | —NH—CO—OCH₃ | |
| 2.27 | Q 27 | —NH—CO—OCH₃ | |
| 2.28 | Q 1 | —NH—CO—O—C₆H₅ | m.p. 141–143° C. |
| 2.29 | Q 2 | —NH—CO—O—C₆H₅ | m.p. 135–136° C. |
| 2.30 | Q 3 | —NH—CO—O—C₆H₅ | |
| 2.31 | Q 4 | —NH—CO—O—C₆H₅ | |
| 2.32 | Q 5 | —NH—CO—O—C₆H₅ | |
| 2.33 | Q 6 | —NH—CO—O—C₆H₅ | |
| 2.34 | Q 7 | —NH—CO—O—C₆H₅ | |
| 2.35 | Q 8 | —NH—CO—O—C₆H₅ | |
| 2.36 | Q 9 | —NH—CO—O—C₆H₅ | |
| 2.37 | Q 10 | —NH—CO—O—C₆H₅ | |
| 2.38 | Q 11 | —NH—CO—O—C₆H₅ | |
| 2.39 | Q 12 | —NH—CO—O—C₆H₅ | |
| 2.40 | Q 13 | —NH—CO—O—C₆H₅ | |
| 2.41 | Q 14 | —NH—CO—O—C₆H₅ | |
| 2.42 | Q 15 | —NH—CO—O—C₆H₅ | |
| 2.43 | Q 16 | —NH—CO—O—C₆H₅ | |
| 2.44 | Q 17 | —NH—CO—O—C₆H₅ | |
| 2.45 | Q 18 | —NH—CO—O—C₆H₅ | |
| 2.46 | Q 19 | —NH—CO—O—C₆H₅ | |
| 2.47 | Q 20 | —NH—CO—O—C₆H₅ | |
| 2.48 | Q 21 | —NH—CO—O—C₆H₅ | |
| 2.49 | Q 22 | —NH—CO—O—C₆H₅ | |
| 2.50 | Q 23 | —NH—CO—O—C₆H₅ | |
| 2.51 | Q 24 | —NH—CO—O—C₆H₅ | |
| 2.52 | Q 25 | —NH—CO—O—C₆H₅ | |
| 2.53 | Q 26 | —NH—CO—O—C₆H₅ | |
| 2.54 | Q 27 | —NH—CO—O—C₆H₅ | |
| 2.55 | Q 1 | —NH—CO—OC₂H₅ | |
| 2.56 | Q 2 | —NH—CO—OC₂H₅ | |
| 2.57 | Q 3 | —NH—CO—OC₂H₅ | |
| 2.58 | Q 4 | —NH—CO—OC₂H₅ | |
| 2.59 | Q 5 | —NH—CO—OC₂H₅ | |
| 2.60 | Q 6 | —NH—CO—OC₂H₅ | |
| 2.61 | Q 7 | —NH—CO—OC₂H₅ | |
| 2.62 | Q 8 | —NH—CO—OC₂H₅ | |
| 2.63 | Q 9 | —NH—CO—OC₂H₅ | |
| 2.64 | Q 10 | —NH—CO—OC₂H₅ | |
| 2.65 | Q 11 | —NH—CO—OC₂H₅ | |
| 2.66 | Q 12 | —NH—CO—OC₂H₅ | |
| 2.67 | Q 13 | —NH—CO—OC₂H₅ | |
| 2.68 | Q 14 | —NH—CO—OC₂H₅ | |
| 2.69 | Q 15 | —NH—CO—OC₂H₅ | |
| 2.70 | Q 16 | —NH—CO—OC₂H₅ | |
| 2.71 | Q 17 | —NH—CO—OC₂H₅ | |
| 2.72 | Q 18 | —NH—CO—OC₂H₅ | |
| 2.73 | Q 19 | —NH—CO—OC₂H₅ | |
| 2.74 | Q 20 | —NH—CO—OC₂H₅ | |
| 2.75 | Q 21 | —NH—CO—OC₂H₅ | |
| 2.76 | Q 22 | —NH—CO—OC₂H₅ | |
| 2.77 | Q 23 | —NH—CO—OC₂H₅ | |
| 2.78 | Q 24 | —NH—CO—OC₂H₅ | |
| 2.79 | Q 25 | —NH—CO—OC₂H₅ | |
| 2.80 | Q 26 | —NH—CO—OC₂H₅ | |
| 2.81 | Q 27 | —NH—CO—OC₂H₅ | |
| 2.82 | Q 28 | —NH—CO—OC₂H₅ | |
| 2.83 | Q 1 | —N=C=O | |
| 2.84 | Q 2 | —N=C=O | |
| 2.85 | Q 3 | —N=C=O | |
| 2.86 | Q 4 | —N=C=O | |
| 2.87 | Q 5 | —N=C=O | |
| 2.88 | Q 6 | —N=C=O | |
| 2.89 | Q 8 | —N=C=O | |
| 2.90 | Q 9 | —N=C=O | |
| 2.91 | Q 10 | —N=C=O | |
| 2.92 | Q 11 | —N=C=O | |
| 2.93 | Q 12 | —N=C=O | |
| 2.94 | Q 13 | —N=C=O | |
| 2.95 | Q 14 | —N=C=O | |
| 2.96 | Q 15 | —N=C=O | |
| 2.97 | Q 16 | —N=C=O | |
| 2.98 | Q 17 | —N=C=O | |
| 2.99 | Q 18 | —N=C=O | |
| 2.100 | Q 19 | —N=C=O | |
| 2.101 | Q 20 | —N=C=O | |
| 2.102 | Q 21 | —N=C=O | |
| 2.103 | Q 22 | —N=C=O | |
| 2.104 | Q 23 | —N=C=O | |
| 2.105 | Q 24 | —N=C=O | |
| 2.106 | Q 25 | —N=C=O | |
| 2.107 | Q 26 | —N=C=O | |
| 2.108 | Q 27 | —N=C=O | |

TABLE 3

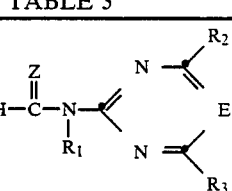

| Compound | Q | Z | E | $R_1$ | $R_2$ | $R_3$ | m.p. [°C.] |
|---|---|---|---|---|---|---|---|
| 3.1 | Q 3 | O | N | H | CH₃ | OCH₃ | |
| 3.2 | Q 3 | O | CH | H | CH₃ | OCH₃ | |
| 3.3 | Q 4 | O | N | H | OCH₃ | OCH₃ | |
| 3.4 | Q 5 | S | N | CH₃ | CH₃ | CH₃ | |
| 3.5 | Q 7 | O | N | H | CH₃ | OCH₃ | |
| 3.6 | Q 6 | O | N | H | CH₃ | OCH₃ | |
| 3.7 | Q 8 | O | N | H | CH₃ | OCH₃ | |
| 3.8 | Q 8 | O | CH | H | CH₃ | OCH₃ | |
| 3.9 | Q 9 | O | N | CH₃ | CH₃ | OCH₃ | |
| 3.10 | Q 10 | O | N | H | CH₃ | OCH₃ | |
| 3.11 | Q 10 | O | CH | H | CH₃ | OCH₃ | |
| 3.12 | Q 11 | O | N | H | OCH₃ | OCH₃ | |
| 3.13 | Q 11 | O | CH | H | CH₃ | OCH₃ | |
| 3.14 | Q 27 | O | N | H | CH₃ | OCH₃ | |
| 3.15 | Q 27 | O | CH | H | CH₃ | OCH₃ | |
| 3.16 | Q 13 | S | N | H | CH₃ | CH₂ | |
| 3.17 | Q 13 | O | CH | H | H | H | |
| 3.18 | Q 18 | O | N | H | OCH₃ | OCH₃ | |
| 3.19 | Q 19 | O | N | CH₃ | CH₃ | CH₃ | |
| 3.20 | Q 18 | O | N | H | CH₃ | OCH₃ | |
| 3.21 | Q 3 | O | CH | H | CH₃ | CH₃ | 160–161 |
| 3.22 | Q 3 | O | N | H | CH₃ | OCH₃ | |
| 3.23 | Q 5 | O | CH | H | CH₃ | OCH₃ | |
| 3.24 | Q 5 | O | N | H | CH₃ | OCH₃ | |
| 3.25 | Q 6 | O | CH | H | CH₃ | OCH₃ | |
| 3.26 | Q 17 | O | N | H | CH₃ | OCH₃ | |
| 3.27 | Q 17 | O | N | H | OCH₃ | OCH₃ | |
| 3.28 | Q 6 | O | N | H | CH₃ | OCH₃ | |
| 3.29 | Q 20 | O | N | CH₃ | CH₃ | CH₃ | |
| 3.30 | Q 7 | S | N | H | CH₃ | OC₃H₇—n | |
| 3.31 | Q 21 | O | N | H | CH₃ | OC₂H₅ | |
| 3.32 | Q 13 | O | N | H | CH₃ | OCH₃ | |
| 3.33 | Q 13 | O | CH | H | CH₃ | OCH₃ | |
| 3.34 | Q 22 | S | CH | CH₃ | CH₃ | CH₃ | |
| 3.35 | Q 23 | O | N | H | OCH₃ | OCH₃ | |
| 3.36 | Q 1 | O | N | H | CH₃ | OCH₃ | 153–154 |
| 3.37 | Q 1 | O | N | H | OCH₃ | N(CH₃)₂ | 154–155 |
| 3.38 | Q 1 | O | N | H | OCH₃ | OC₂H₅ | |
| 3.39 | Q 1 | O | N | H | OCH₃ | OCH(CH₃)₂ | |
| 3.40 | Q 1 | O | N | H | OCH₃ | OCH₂CF₃ | |
| 3.41 | Q 1 | O | N | H | C₂H₅ | OCH₃ | 139–141 |
| 3.42 | Q 1 | O | N | H | OC₂H₅ | OC₂H₅ | |
| 3.43 | Q 1 | O | N | H | SCH₃ | OCH₃ | |
| 3.44 | Q 1 | O | N | H | CH₃ | OC₂H₅ | 143–144 |
| 3.45 | Q 1 | O | CH | H | CH₃ | CH₃ | 165– |

TABLE 3-continued

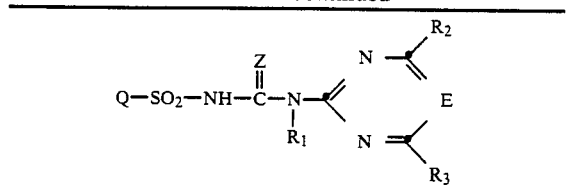

| Compound | Q | Z | E | $R_1$ | $R_2$ | $R_3$ | m.p. [°C.] |
|---|---|---|---|---|---|---|---|
| 3.46 | Q 1 | O | CH | H | $CH_3$ | $OCH_3$ | 167 |
| 3.47 | Q 1 | O | CH | H | $CH_3$ | $OCHF_2$ | 138–141 |
| 3.48 | Q 1 | O | CH | H | $CH_3$ | $N(CH_3)_2$ | 142–145 |
| 3.49 | Q 1 | O | CH | H | $OCH_3$ | $OCH_3$ | 160–163 |
| 3.50 | Q 1 | O | CH | H | $OCHF_2$ | $OCHF_2$ | |
| 3.51 | Q 1 | O | CH | H | $OCH_3$ | $OCHF_2$ | |
| 3.52 | Q 1 | O | CH | H | $OCH_3$ | Cl | |
| 3.53 | Q 1 | O | CH | H | $OCH_3$ | F | |
| 3.54 | Q 1 | O | CH | H | $OCH_3$ | $N(CH_3)_2$ | |
| 3.55 | Q 1 | O | CH | H | $CH_2F$ | $OCH_3$ | |
| 3.56 | Q 1 | O | CH | H | $OCHF_2$ | $N(CH_3)_2$ | |
| 3.57 | Q 1 | O | CH | H | $OCH_3$ | $OCF_2-CHF_2$ | |
| 3.58 | Q 1 | O | CH | H | $CH_3$ | $OCF_2-CHF_2$ | |
| 3.59 | Q 2 | O | N | H | $CH_3$ | $OCH_3$ | 135–137 |
| 3.60 | Q 2 | O | N | H | $OCH_3$ | $N(CH_3)_2$ | 180–181 |
| 3.61 | Q 2 | O | N | H | OCH | $OC_2H_5$ | |
| 3.62 | Q 2 | O | N | H | $OCH_3$ | $OCH(CH_3)_2$ | |
| 3.63 | Q 2 | O | N | H | $OCH_3$ | $OCH_2CF_3$ | |
| 3.64 | Q 2 | O | N | H | $C_2H_5$ | $OCH_3$ | 122–124 |
| 3.65 | Q 2 | O | N | H | $OC_2H_5$ | $OC_2H_5$ | |
| 3.66 | Q 2 | O | N | H | $SCH_3$ | $OCH_3$ | |
| 3.67 | Q 2 | O | N | H | $CH_3$ | $OC_2H_5$ | 123–125 |
| 3.68 | Q 2 | O | CH | H | $CH_3$ | $CH_3$ | 166–167 |
| 3.69 | Q 2 | O | CH | H | $CH_3$ | $OCH_3$ | 139–141 |
| 3.70 | Q 2 | O | CH | H | $CH_3$ | $OCHF_2$ | 116–123 |
| 3.71 | Q 2 | O | CH | H | $CH_3$ | $N(CH_3)_2$ | |
| 3.72 | Q 2 | O | CH | H | $OCH_3$ | $OCH_3$ | 143–147 |
| 3.73 | Q 2 | O | CH | H | $OCHF_2$ | $OCHF_2$ | |
| 3.74 | Q 2 | O | CH | H | $OCH_3$ | $OCHF_2$ | |
| 3.75 | Q 2 | O | CH | H | $OCH_3$ | Cl | |
| 3.76 | Q 2 | O | CH | H | $OCH_3$ | F | |
| 3.77 | Q 2 | O | CH | H | $OCH_3$ | $N(CH_3)_2$ | |
| 3.78 | Q 2 | O | CH | H | $CH_2F$ | $OCH_3$ | |
| 3.79 | Q 2 | O | CH | H | $OCHF_2$ | $N(CH_3)_2$ | |
| 3.80 | Q 2 | O | CH | H | $OCH_3$ | $OCF_2-CHF_2$ | |
| 3.81 | Q 2 | O | CH | H | $CH_3$ | $OCF_2-CHF_2$ | |
| 3.82 | Q 14 | O | N | H | $CH_3$ | $OCH_3$ | |
| 3.83 | Q 14 | O | CH | H | $CH_3$ | $OCH_3$ | |
| 3.84 | Q 14 | O | CH | H | $CH_3$ | $CH_3$ | |
| 3.85 | Q 14 | O | CH | H | $OCH_3$ | $OCH_3$ | |
| 3.86 | Q 14 | O | CH | H | $CH_3$ | $OCHF_2$ | |
| 3.87 | Q 24 | O | N | H | $CH_3$ | $OCH_3$ | |
| 3.88 | Q 24 | O | CH | H | $CH_3$ | $OCH_3$ | |
| 3.89 | Q 24 | O | CH | H | $CH_3$ | $OCHF_2$ | |
| 3.90 | Q 25 | O | N | H | $CH_3$ | $OCH_3$ | |
| 3.91 | Q 25 | O | CH | H | $CH_3$ | $OCH_3$ | |
| 3.92 | Q 26 | O | N | H | $CH_3$ | $OCH_3$ | |
| 3.93 | Q 26 | O | CH | H | $CH_3$ | $OCH_3$ | |
| 3.94 | Q 15 | O | CH | H | $CH_3$ | $OCH_3$ | |
| 3.95 | Q 15 | O | N | H | $CH_3$ | $OCH_3$ | |
| 3.96 | Q 15 | O | CH | H | $CH_3$ | $OCHF_2$ | |
| 3.97 | Q 16 | O | N | H | $CH_3$ | $OCH_3$ | |
| 3.98 | Q 16 | O | CH | H | $CH_3$ | $OCH_3$ | |
| 3.99 | Q 17 | O | N | H | $CH_3$ | $OCH_3$ | |
| 3.100 | Q 17 | O | CH | H | $CH_3$ | $OCH_3$ | |
| 3.101 | Q 27 | O | N | H | $OCH_3$ | $OC_2H_5$ | |
| 3.102 | Q 27 | O | N | H | $OCH_3$ | $OCH(CH_3)_2$ | |
| 3.103 | Q 27 | O | N | H | $CH_3$ | $OCH_3$ | |
| 3.104 | Q 27 | O | N | H | $OCH_3$ | $N(CH_3)_2$ | |
| 3.105 | Q 27 | O | N | H | $OCH_3$ | $OCH_2CF_3$ | |
| 3.106 | Q 27 | O | N | H | $C_2H_5$ | $OCH_3$ | |
| 3.107 | Q 27 | O | N | H | $OCH_3$ | $OCH_3$ | |
| 3.108 | Q 27 | O | N | H | $CH_3$ | $OC_2H_5$ | |
| 3.109 | Q 27 | O | CH | H | $CH_3$ | $CH_3$ | |
| 3.110 | Q 27 | O | CH | H | $CH_3$ | $OCH_3$ | |
| 3.111 | Q 27 | O | CH | $CH_3$ | $CH_3$ | $OC_2H_5$ | |
| 3.112 | Q 27 | O | CH | H | $OCH_3$ | $OCH_3$ | |
| 3.113 | Q 27 | O | CH | H | $OCHF_2$ | $OCHF_2$ | |
| 3.114 | Q 27 | O | CH | H | $OCH_3$ | $OCHF_2$ | |
| 3.115 | Q 30 | O | N | H | $OCH_3$ | $OC_2H_5$ | |
| 3.116 | Q 30 | O | N | H | $OCH_3$ | $OCH(CH_3)_2$ | |
| 3.117 | Q 30 | O | N | H | $CH_3$ | $OCH_3$ | |
| 3.118 | Q 30 | O | N | H | $OCH_3$ | $N(CH_3)_2$ | |
| 3.119 | Q 30 | O | N | H | $OCH_3$ | $OCH_2CF_3$ | |
| 3.120 | Q 30 | O | N | H | $C_2H_5$ | $OCH_3$ | |
| 3.121 | Q 30 | O | N | H | $OCH_3$ | $OCH_3$ | |
| 3.122 | Q 30 | O | N | H | $CH_3$ | $OC_2H_5$ | |
| 3.123 | Q 30 | O | CH | H | $CH_3$ | $CH_3$ | |
| 3.124 | Q 30 | O | CH | H | $CH_3$ | $OCH_3$ | |
| 3.125 | Q 30 | O | CH | H | $CH_3$ | $OCHF_2$ | |
| 3.126 | Q 30 | O | CH | H | $OCH_3$ | $OCH_3$ | |
| 3.127 | Q 30 | O | CH | H | $OCHF_2$ | $OCHF_2$ | |
| 3.128 | Q 30 | O | CH | H | $OCH_3$ | $OCHF_2$ | |
| 3.129 | Q 32 | O | N | H | $OCH_3$ | $OC_2H_5$ | |
| 3.130 | Q 32 | O | N | H | $OCH_3$ | $OCH(CH_3)_2$ | |
| 3.131 | Q 32 | O | N | H | $CH_3$ | $OCH_3$ | |
| 3.132 | Q 32 | O | N | H | $OCH_3$ | $N(CH_3)_2$ | |
| 3.133 | Q 32 | O | N | H | $OCH_3$ | $OCH_2CF_3$ | |
| 3.134 | Q 32 | O | N | H | $C_2H_5$ | $OCH_3$ | |
| 3.135 | Q 32 | O | N | H | $OCH_3$ | $OCH_3$ | |
| 3.136 | Q 32 | O | N | H | $CH_3$ | $OC_2H_5$ | |
| 3.137 | Q 32 | O | CH | H | $CH_3$ | $CH_3$ | |
| 3.138 | Q 32 | O | CH | H | $CH_3$ | $OCH_3$ | |
| 3.139 | Q 32 | O | CH | H | $CH_3$ | $OCHF_2$ | |
| 3.140 | Q 32 | O | CH | H | $OCH_3$ | $OCH_3$ | |
| 3.141 | Q 32 | O | CH | H | $OCHF_2$ | $OCHF_2$ | |
| 3.142 | Q 32 | O | CH | H | $OCH_3$ | $OCHF_2$ | |
| 3.143 | Q 33 | O | N | H | $OCH_3$ | $OC_2H_5$ | |
| 3.144 | Q 33 | O | N | H | $OCH_3$ | $OCH(CH_3)_2$ | |
| 3.145 | Q 33 | O | N | H | $CH_3$ | $OCH_3$ | |
| 3.146 | Q 33 | O | N | H | $OCH_3$ | $N(CH_3)_2$ | |
| 3.147 | Q 33 | O | N | H | $OCH_3$ | $OCH_2CF_3$ | |
| 3.148 | Q 33 | O | N | H | $C_2H_5$ | $OCH_3$ | |
| 3.149 | Q 33 | O | N | H | $OCH_3$ | $OCH_3$ | |
| 3.150 | Q 33 | O | N | H | $CH_3$ | $OC_2H_5$ | |
| 3.151 | Q 33 | O | CH | H | $CH_3$ | $CH_3$ | |
| 3.152 | Q 33 | O | CH | H | $CH_3$ | $OCH_3$ | |
| 3.153 | Q 33 | O | CH | H | $CH_3$ | $OCHF$ | |
| 3.154 | Q 33 | O | CH | H | $CH_3$ | $OCHF_2$ | |
| 3.155 | Q 33 | O | CH | H | $OCHF_2$ | $OCHF_2$ | |
| 3.156 | Q 33 | O | CH | H | $OCH_3$ | $OCHF_2$ | |
| 3.157 | Q 34 | O | N | H | $OCH_3$ | $OC_2H_5$ | |
| 3.158 | Q 34 | O | N | H | $OCH_3$ | $OCH(CH_3)_2$ | |
| 3.159 | Q 34 | O | N | H | $CH_3$ | $OCH_3$ | |
| 3.160 | Q 34 | O | N | H | $OCH_3$ | $N(CH_3)_2$ | |
| 3.161 | Q 34 | O | N | H | $OCH_3$ | $OCH_2CF_3$ | |
| 3.162 | Q 34 | O | N | H | $C_2H_5$ | $OCH_3$ | |
| 3.163 | Q 34 | O | N | H | $OCH_3$ | $OCH_3$ | |
| 3.164 | Q 34 | O | N | H | $CH_3$ | $OC_2H_5$ | |
| 3.165 | Q 34 | O | CH | H | $CH_3$ | $CH_3$ | |
| 3.166 | Q 34 | O | CH | H | $CH_3$ | $OCH_3$ | |
| 3.167 | Q 34 | O | CH | H | $CH_3$ | $OCHF_2$ | |
| 3.168 | Q 34 | O | CH | H | $OCH_3$ | $OCH_3$ | |
| 3.169 | Q 34 | O | CH | H | $OCHF_2$ | $OCHF_2$ | |
| 3.170 | Q 34 | O | CH | H | $OCH_3$ | $OCHF_2$ | |
| 3.171 | Q 37 | O | N | H | $OCH_3$ | $OC_2H_5$ | |
| 3.172 | Q 37 | O | N | H | $OCH_3$ | $OCH(CH_3)_2$ | |
| 3.173 | Q 37 | O | N | H | $CH_3$ | $OCH_3$ | |
| 3.174 | Q 37 | O | N | H | $OCH_3$ | $N(CH_3)_2$ | |
| 3.175 | Q 37 | O | N | H | $OCH_3$ | $OCH_2CF_3$ | |

TABLE 3-continued

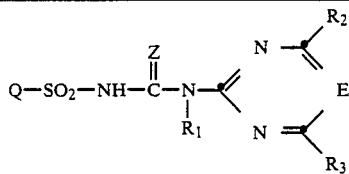

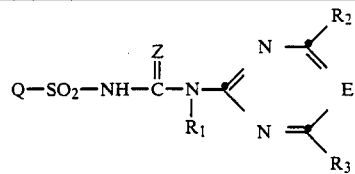

| Compound | Q | Z | E | R₁ | R₂ | R₃ | m.p. [°C.] |
|---|---|---|---|---|---|---|---|
| 3.176 | Q 37 | O | N | H | C₂H₅ | OCH₃ | |
| 3.177 | Q 37 | O | N | H | OCH₃ | OCH₃ | |
| 3.178 | Q 37 | O | N | H | CH₃ | OC₂H₅ | |
| 3.179 | Q 37 | O | CH | H | CH₃ | CH₃ | |
| 3.180 | Q 37 | O | CH | H | CH₃ | OCH₃ | |
| 3.181 | Q 37 | O | CH | H | CH₃ | OCHF₂ | |
| 3.182 | Q 37 | O | CH | H | OCH₃ | OCH₃ | |
| 3.183 | Q 37 | O | CH | H | OCHF₂ | OCHF₂ | |
| 3.184 | Q 37 | O | CH | H | OCH₃ | OCHF₂ | |
| 3.185 | Q 38 | O | N | H | OCH₃ | OC₂H₅ | |
| 3.186 | Q 38 | O | N | H | OCH₃ | OCH(CH₃)₂ | |
| 3.187 | Q 38 | O | N | H | CH₃ | OCH₃ | |
| 3.188 | Q 38 | O | N | H | OCH₃ | N(CH₃)₂ | |
| 3.189 | Q 38 | O | N | H | OCH₃ | OCH₂CF₃ | |
| 3.190 | Q 38 | O | N | H | C₂H₅ | OCH₃ | |
| 3.191 | Q 38 | O | N | H | OCH₃ | OCH₃ | |
| 3.192 | Q 38 | O | N | H | CH₃ | OC₂H₅ | |
| 3.193 | Q 38 | O | CH | H | CH₃ | CH₃ | |
| 3.194 | Q 38 | O | CH | H | CH₃ | OCH₃ | |
| 3.195 | Q 38 | O | CH | H | CH₃ | OCHF₂ | |
| 3.196 | Q 38 | O | CH | H | OCH₃ | OCH₃ | |
| 3.197 | Q 38 | O | CH | H | OCHF₂ | OCHF₂ | |
| 3.198 | Q 38 | O | CH | H | OCH₃ | OCHF₂ | |
| 3.199 | Q 39 | O | N | H | OCH₃ | OC₂H₅ | |
| 3.200 | Q 39 | O | N | H | OCH₃ | OCH(CH₃)₂ | |
| 3.201 | Q 39 | O | N | H | CH₃ | OCH₃ | |
| 3.202 | Q 39 | O | N | H | OCH₃ | N(CH₃)₂ | |
| 3.203 | Q 39 | O | N | H | OCH₃ | OCH₂CF₃ | |
| 3.204 | Q 39 | O | N | H | C₂H₅ | OCH₃ | |
| 3.205 | Q 39 | O | N | H | OCH₃ | OCH₃ | |
| 3.206 | Q 39 | O | N | H | CH₃ | OC₂H₅ | |
| 3.207 | Q 39 | O | CH | H | CH₃ | CH₃ | |
| 3.208 | Q 39 | O | CH | H | CH₃ | OCH₃ | |
| 3.209 | Q 39 | O | CH | H | CH₃ | OCHF₂ | |
| 3.210 | Q 39 | O | CH | H | OCH₃ | OCH₃ | |
| 3.211 | Q 39 | O | CH | H | OCHF₂ | OCHF₂ | |
| 3.212 | Q 39 | O | CH | H | OCH₃ | OCHF₂ | |
| 3.213 | Q 28 | O | N | H | CH₃ | OCH₃ | |
| 3.214 | Q 28 | O | N | H | OCH₃ | N(CH₃)₂ | |
| 3.215 | Q 28 | O | N | H | OCH₃ | OC₂H₅ | |
| 3.216 | Q 28 | O | N | H | OCH₃ | OCH(CH₃)₂ | |
| 3.217 | Q 28 | O | N | H | OCH₃ | OCH₂CF₃ | |
| 3.218 | Q 28 | O | N | H | C₂H₅ | OCH₃ | |
| 3.219 | Q 28 | O | N | H | OC₂H₅ | OC₂H₅ | |
| 3.220 | Q 28 | O | N | H | SCH₃ | OCH₃ | |
| 3.221 | Q 28 | O | N | H | CH₃ | OC₂H₅ | |
| 3.222 | Q 28 | O | CH | H | CH₃ | CH₃ | |
| 3.223 | Q 28 | O | CH | H | CH₃ | OCH₃ | |
| 3.224 | | O | CH | H | CH₃ | OCHF₂ | |
| 3.225 | Q 38 | O | CH | H | CH₃ | N(CH₃)₂ | |
| 3.226 | Q 28 | O | CH | H | OCH₃ | OCH₃ | |
| 2.227 | Q 28 | O | CH | H | OCHF₂ | OCHF₂ | |
| 3.228 | Q 28 | O | CH | H | OCH₃ | OCHF₂ | |
| 3.229 | Q 28 | O | CH | H | OCH₃ | Cl | |
| 3.230 | Q 28 | O | CH | H | OCH₃ | F | |
| 3.231 | Q 28 | O | CH | H | OCH₃ | N(CH₃)₂ | |
| 3.232 | Q 28 | O | CH | H | CH₂F | OCH₃ | |
| 3.233 | Q 28 | O | CH | H | OCHF₂ | N(CH₃)₂ | |
| 3.234 | Q 28 | O | CH | H | OCH₃ | OCF₂—CHF₂ | |
| 3.235 | Q 28 | O | CH | H | CH₃ | OCF₂—CHF₂ | |
| 3.236 | Q 29 | O | N | H | CH₃ | OCH₃ | |
| 3.237 | Q 29 | O | N | H | OCH₃ | N(CH₃)₂ | |
| 3.238 | Q 29 | O | N | H | OCH₃ | OC₂H₅ | |
| 3.239 | Q 29 | O | N | H | OCH₃ | OCH(CH₃)₂ | |
| 3.240 | Q 29 | O | N | H | OCH₃ | OCH₂CF₃ | |
| 3.241 | Q 29 | O | N | H | C₂H₅ | OCH₃ | |
| 3.242 | Q 29 | O | N | H | OC₂H₅ | OC₂H₅ | |
| 3.243 | Q 29 | O | N | H | SCH₃ | OCH₃ | |
| 3.244 | Q 29 | O | N | H | CH₃ | OC₂H₅ | |
| 3.245 | Q 29 | O | CH | H | CH₃ | CH₃ | |
| 3.246 | Q 29 | O | CH | H | CH₃ | OCH₃ | |
| 3.247 | Q 29 | O | CH | H | CH₃ | OCHF₂ | |
| 3.248 | Q 29 | O | CH | H | CH₃ | N(CH₃)₂ | |
| 3.249 | Q 29 | O | CH | H | OCH₃ | OCH₃ | |
| 3.250 | Q 29 | O | CH | H | OCHF₂ | OCHF₂ | |
| 3.251 | Q 29 | O | CH | H | OCH₃ | OCHF₂ | |
| 3.252 | Q 29 | O | CH | H | OCH₃ | Cl | |
| 3.253 | Q 29 | O | CH | H | OCH₃ | F | |
| 3.254 | Q 29 | O | CH | H | OCH₃ | N(CH₃)₂ | |
| 3.255 | Q 29 | O | CH | H | CH₂F | OCH₃ | |
| 3.256 | Q 29 | O | CH | H | OCHF₂ | N(CH₃)₂ | |
| 3.257 | Q 29 | O | CH | H | OCH₃ | OCF₂—CHF₂ | |
| 3.258 | Q 29 | O | CH | H | CH₃ | OCF₂—CHF₂ | |
| 3.259 | Q 31 | O | N | H | CH₃ | OCH₃ | |
| 3.260 | Q 31 | O | N | H | OCH₃ | N(CH₃)₂ | |
| 3.261 | Q 31 | O | N | H | OCH₃ | OC₂H₅ | |
| 3.262 | Q 31 | O | N | H | OCH₃ | OCH(CH₃)₂ | |
| 3.263 | Q 31 | O | N | H | OCH₃ | OCH₂CF₃ | |
| 3.264 | Q 31 | O | N | H | C₂H₅ | OCH₃ | |
| 3.265 | Q 31 | O | N | H | OC₂H₅ | OC₂H₅ | |
| 3.266 | Q 31 | O | N | H | SCH₃ | OCH₃ | |
| 3.267 | Q 31 | O | N | H | CH₃ | OC₂H₅ | |
| 3.268 | Q 31 | O | CH | H | CH₃ | CH₃ | |
| 3.269 | Q 31 | O | CH | H | CH₃ | OCH₃ | |
| 3.270 | Q 31 | O | CH | H | CH₃ | OCHF₂ | |
| 3.271 | Q 31 | O | CH | H | CH₃ | N(CH₃)₂ | |
| 3.272 | Q 31 | O | CH | H | OCH₃ | OCH₃ | |
| 3.273 | Q 31 | O | CH | H | OCHF₂ | OCHF₂ | |
| 3.274 | Q 31 | O | CH | H | OCH₃ | OCHF₂ | |
| 3.275 | Q 31 | O | CH | H | OCH₃ | Cl | |
| 3.276 | Q 31 | O | CH | H | OCH₃ | F | |
| 3.277 | Q 31 | O | CH | H | OCH₃ | N(CH₃)₂ | |
| 3.278 | Q 31 | O | CH | H | CH₂F | OCH₃ | |
| 3.279 | Q 31 | O | CH | H | OCHF₂ | N(CH₃)₂ | |
| 3.280 | Q 31 | O | CH | H | OCH₃ | OCF₂—CHF₂ | |
| 3.281 | Q 31 | O | CH | H | CH₃ | OCF₂—CHF₂ | |
| 3.282 | Q 35 | O | N | H | CH₃ | OCH₃ | |
| 3.283 | Q 35 | O | N | H | OCH₃ | N(CH₃)₂ | |
| 3.284 | Q 35 | O | N | H | OCH₃ | OC₂H₅ | |
| 3.285 | Q 35 | O | N | H | OCH₃ | OCH(CH₃)₂ | |
| 3.286 | Q 35 | O | N | H | OCH₃ | OCH₂CF₃ | |
| 3.287 | Q 35 | O | N | H | C₂H₅ | OCH₃ | |
| 3.288 | Q 35 | O | N | H | OC₂H₅ | OC₂H₅ | |
| 3.289 | Q 35 | O | N | H | SCH₃ | OCH₃ | |
| 3.290 | Q 35 | O | N | H | CH₃ | OC₂H₅ | |
| 3.291 | Q 35 | O | CH | H | CH₃ | CH₃ | |
| 3.292 | Q 35 | O | CH | H | CH₃ | OCH₃ | |
| 3.293 | Q 35 | O | CH | H | CH₃ | OCHF₂ | |
| 3.294 | Q 35 | O | CH | H | CH₃ | N(CH₃)₂ | |
| 3.295 | Q 35 | O | CH | H | OCH₃ | OCH₃ | |
| 3.296 | Q 35 | O | CH | H | OCHF₂ | OCHF₂ | |
| 3.297 | Q 35 | O | CH | H | OCH₃ | OCHF₂ | |
| 3.298 | Q 35 | O | CH | H | OCH₃ | Cl | |
| 3.299 | Q 35 | O | CH | H | OCH₃ | F | |
| 3.300 | Q 35 | O | CH | H | OCH₃ | N(CH₃)₂ | |
| 3.301 | Q 35 | O | CH | H | CH₂F | OCH₃ | |
| 3.303 | A 35 | O | CH | H | OCHF₂ | N(CH₃)₂ | |
| 3.304 | Q 35 | O | CH | H | OCH₃ | OCF₂—CHF₂ | |
| 3.305 | Q 35 | O | CH | H | CH₃ | OCF₂—CHF₂ | |
| 3.306 | Q 1 | O | N | H | OCH₃ | OCH₃ | 142–143 |
| 3.307 | Q 2 | O | N | H | OCH₃ | OCH₃ | 124–126 |
| 3.308 | Q 36 | O | N | H | CH₃ | OCH₃ | |
| 3.309 | Q 36 | O | N | H | OCH₃ | N(CH₃)₂ | |
| 3.310 | Q 36 | O | N | H | OCH₃ | OC₂H₅ | |
| 3.311 | Q 36 | O | N | H | OCH₃ | OCH(CH₃)₂ | |
| 3.312 | Q 36 | O | N | H | OCH₃ | OCH₂CF₃ | |
| 3.313 | Q 36 | O | N | H | C₂H₅ | OCH₃ | |
| 3.314 | Q 36 | O | N | H | OC₂H₅ | OC₂H₅ | |
| 3.315 | Q 36 | O | N | H | SCH₃ | OCH₃ | |
| 3.316 | Q 36 | O | N | H | CH₃ | OC₂H₅ | |

TABLE 3-continued $$Q-SO_2-NH-\overset{Z}{\underset{\parallel}{C}}-\underset{R_1}{N}-\overset{R_2}{\underset{N=}{N=}}\overset{}{\underset{R_3}{\diagdown}} E$$

| Com-pound | Q | Z | E | R₁ | R₂ | R₃ | m.p. [°C.] |
|---|---|---|---|---|---|---|---|
| 3.317 | Q 36 | O | CH | H | CH₃ | CH₃ | |
| 3.318 | Q 36 | O | CH | H | CH₃ | OCH₃ | |
| 3.319 | Q 36 | O | CH | H | CH₃ | OCHF₂ | |
| 3.320 | Q 36 | O | CH | H | CH₃ | N(CH₃)₂ | |
| 3.321 | A 36 | O | CH | H | OCH₃ | OCH₃ | |
| 3.322 | Q 36 | O | CH | H | OCHF₂ | OCHF₂ | |
| 3.323 | Q 36 | O | CH | H | OCH₃ | OCHF₂ | |
| 3.324 | Q 36 | O | CH | H | OCH₃ | Cl | |
| 3.325 | Q 36 | O | CH | H | OCH₃ | F | |
| 3.326 | Q 36 | O | CH | H | OCH₃ | N(CH₃)₂ | |
| 3.327 | Q 36 | O | CH | H | CH₂F | OCH₃ | |
| 3.328 | Q 36 | O | CH | H | OCHF₂ | N(CH₃)₂ | |
| 3.329 | Q 36 | O | CH | H | OCH₃ | OCF₂—CHF₂ | |
| 3.330 | Q 36 | O | CH | H | CH₃ | OCF₂—CHF₂ | |

For application, the compounds of formula I can be processed to the following formulations.

FORMULATION EXAMPLES

EXAMPLE 2

Formulation examples for compounds of formula I (percentages are by weight)

| (a) Wettable powders | (a) | (b) | (c) |
|---|---|---|---|
| compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7-8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| compound of formula I | 10% | 1% |
| octylphenol polyethylene glycol ether (4-5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of formula I | 0.1% | 1% |
| talcum | 99.9% | — |
| kaolin | — | 99% |

Ready for use dusts are obtained by mixing the active ingredient with the carriers, and grinding the mixture in a suitable mill.

| (d) Extruder granulate | (a) | (b) |
|---|---|---|
| compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of formula I | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspension of any desired concentration can be obtained by dilution with water.

| (g) Salt solution | |
|---|---|
| compound of formula | 5% |
| isopropylamine | 1% |
| octylphenol polyethylene glycol ether (78 moles of ethylene oxide) | 3% |
| water | 91% |

Emulsions of the desired concentration may be prepared from such concentrates by dilution with water. These emulsions are particularly suitable for foliar application. In addition it is possible to prepare further wettable powders with other mixture ratios or other carriers and adjuvants customarily employed in formulation technology. The active ingredients are intimately mixed with the adjuvants in suitable mixers and ground in corresponding mills and rollers to give wettable powders of excellent wettability and suspension power which can in turn be diluted with water to give suspensions of the desired concentration which are particularly suitable for foliar application. The invention also relates to such compositions.

Compositions which are formulated in the manner described above and which contain one of the compounds of Table I can be successfully used for growth regulation and/or for herbicidal application.

BIOLOGICAL EXAMPLES

EXAMPLE 3

Preemergence herbicidal action

In a greenhouse, plant seeds are sown in flower pots of 12-15 cm diameter. Immediately after sowing, the surface of the soil is treated with an aqueous dispersion or solution of the compounds to be tested. Concentrations of 4 kg a.i./ha are employed. The pots are then kept in the greenhouse at 22°-25° C. and 50-70% relative humidity. The test is evaluated 3 weeks later. The compounds of formula I are very effective in this test, i.e. the test plants are irreversibly damaged so that they die or wither.

EXAMPLE 4

Postemergence herbicidal action (contact action)

A large number of weeds and cultivated plants, both monocots and dicots, are sprayed postemergence in the 4- to 6-leaf stage with an aqueous dispersion of test compound at a rate of application of 4 kg a.i./ha, and then kept at 24°-26° C. and 45-60% relative humidity. The test is evaluated 15 days after treatment. The compounds of formula I have good herbicidal action in this test.

EXAMPLE 5

Growth inhibition of cereals

Summar barley (*Hordeum vulgare*) and summer rye (Secale) are sown in sterilised soil in plastic beakers in a greenhouse and watered as required. The cereal shoots are treated about 21 days after sowing with an aqueous spray mixture of a compound of the formula I. The concentration corresponds to 0.5 and 2.5 kg respectively of active ingredient per hectare. Evaluation of the growth of the cereals is made 10 and 21 days after application. A comparison with untreated controls shows that the growth of cereal plants treated with compounds of the formula I is significantly reduced.

EXAMPLE 6

Growth inhibition of grasses

Seeds of the grasses *Lolium perenne, Poa pratensis, Festuca ovina,* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of the formula I. The concentration of test compound corresponds to a rate of application of 2.5 kg per hectare. The growth of the grasses is evaluated 10 and 21 days after application. The evaluation shows that the compounds of Table 1 effect a significant reduction in growth.

What is claimed is:

1. A pyrimidin-5-sulfonamide of the formula

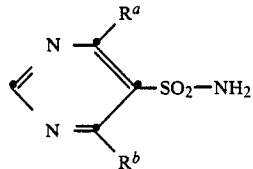

wherein
  $R^a$ is hydrogen, halogen, $C_{1-4}$alkyl or $C_1$-$C_4$alkoxy, and
  $R^b$ is halogen, $C_1$-$C_4$alkyl, $C_1C_4$alkoxy, $C_1$-$C_4$alkoxycarbonyl, $C_1$-$C_4$alkylaminocarbonyl, di($C_1$-$C_4$alkyl)aminocarbonyl or trifluoromethyl.

2. A compound according to claim 20, wherein $R^a$ is hydrogen, chlorine or methoxy and $R^b$ is chlorine, methoxy or trifluoromethyl.

3. 4,6-Dimethoxy-5-pyrimidinylsulfonamide according to claim 1.

* * * * *